United States Patent [19]

Spivack

[11] Patent Number: 4,692,539
[45] Date of Patent: Sep. 8, 1987

[54] PENTAERYTHRITOL DIPHOSPHITE STABILIZERS AND PROCESS

[75] Inventor: John D. Spivack, Spring Valley, N.Y.
[73] Assignee: Ciba-Geigy Corporation, Ardsley, N.Y.
[21] Appl. No.: 922,803
[22] Filed: Oct. 24, 1986

Related U.S. Application Data

[62] Division of Ser. No. 685,370, Dec. 24, 1984, abandoned.

[51] Int. Cl.⁴ .............................. C07F 9/15; C08K 5/52
[52] U.S. Cl. ..................................... 558/78; 524/120
[58] Field of Search ............................................. 558/78

[56] References Cited

U.S. PATENT DOCUMENTS

| | | | |
|---|---|---|---|
| 3,192,243 | 6/1965 | Gagiiani | 558/78 |
| 3,265,774 | 8/1966 | Friedman | 558/78 |
| 4,094,855 | 6/1978 | Spivack | 524/120 |
| 4,143,101 | 3/1979 | Mayerhoefer et al. | 558/78 |
| 4,180,498 | 12/1979 | Spivack | 524/120 |
| 4,207,229 | 6/1980 | Spivack | 524/120 |
| 4,290,976 | 9/1981 | Hechenbleikner et al. | 558/78 |
| 4,305,866 | 12/1981 | York et al. | 558/78 |
| 4,371,647 | 2/1983 | Minagawa et al. | 524/120 |

FOREIGN PATENT DOCUMENTS 159294  10/1985  European Pat. Off. .............. 558/78

Primary Examiner—Morton Foelak
Assistant Examiner—Kriellion Morgan
Attorney, Agent, or Firm—Harry Falber

[57] ABSTRACT

Pentaerythritol diphosphites corresponding to the formula

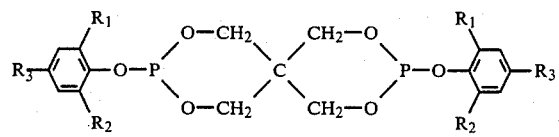

being useful for stabilizing organic materials against thermal, oxidative and actinic degradation and a process for the preparation thereof.

6 Claims, No Drawings

PENTAERYTHRITOL DIPHOSPHITE STABILIZERS AND PROCESS

This application is a division of application Ser. No. 685,370, filed 12/24/84 now abandoned.

Organic polymeric materials such as plastics and resins, are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various pentaerythritol diphosphite stabilizers have been disclosed in the prior art. Bis(phenyl)pentaerythritol diphosphites were disclosed in early patents such as U.S. Pat. No. 2,847,443 and British Pat. No. 1,180,398. A summary of such diphosphites can be found in U.S. Pat. Nos. 4,302,383 and 4,305,866 wherein various bis(alkyl)-, (phenyl)- and (alkyphenyl)-pentaerythritol diphoshites are disclosed.

U.S. Pat. No. 4,180,498 generically discloses and claims bis(ester-substituted phenyl) pentaerythritol diphoshites. The ester grouping is identified by the notation "—(A)q—COOR$_4$" where A is C$_1$-C$_3$ alkylene, q is 0 or 1 and R$_4$ is C$_1$-C$_{24}$ alkyl, phenyl or alkylsubstituted phenyl. Such compounds are not specifically exemplified, the closest exemplified species being the mono-ester compounds. These compounds are noted to have the capability of stabilizing organic materials against thermal, oxidative and ultraviolet light degradation. While such activity is exhibited by the mono-esters, more effective performance in terms of antioxidant activity, duration of activity resulting from prolonged stabilizer presence and hydrolytic stability is dictated by commercial requirements.

Accordingly, it is the primary object of this invention to identify and provide a select class of bis(ester-substituted phenyl)pentaerythritol diphosphites which exhibit a broad range of stabilization performance characteristics.

It is a further object to provide such a class which unexpectedly improves upon the performance characteristics of the diphosphites specifically exemplified in the prior art.

It is another object to provide an efficient, effective process for preparing pentaerythritol diphosphites, including the compounds of this invention.

Various other objects and advantages of this invention will become evident from the following description thereof.

It has now been surprisingly determined that the bis(ester substituted phenyl)pentaerythritol diphosphites having either C$_1$ or C$_{12}$-C$_{18}$ ester substituents exhibit a variety of desirable properties which makes them particularly effective and useful as stabilizers in a broad range of substrates. Of primary significance, these compounds exhibit excellent antioxidant activity in diverse substrates, provide a longer period of effectiveness as a result of their prolonged presence in the substrate and exhibit increased hydrolytic stability. The latter property is most meaningful in view of the hot, humid storage conditions often encountered by commercial chemical compounds. It is particularly in these areas that the compounds of this invention improve upon the performance characteristics of the mono-esters disclosed in U.S. Pat. No. 4,180,498.

It has also been determined that the presence of catalytic amounts of mono- or polyalkylene glycol ether complexing agents during the reaction of the appropriate alcohol or phenol with 3,9-dichloro-2,4,8,10-tetraoxa-3,9-diphos- phaspiro-[5,5]undecane to produce pentaerythritol diphosphites results in an improved preparative process. Thus, yields of product are increased as a result of the conversion of the phenol to the phenolate anion and the increased reactivity of the phenolate anion. In this manner, the process is also readily available for the reaction of phenolic groups which are highly hindered by ortho alkyl groups.

The compounds of this invention correspond to the formula

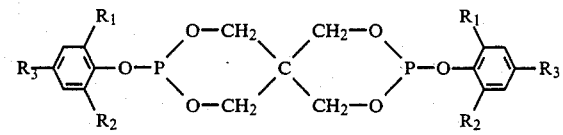

wherein
R$_1$ and R$_2$ are independently lower alkyl of 1 to 8 carbon atoms,
R$_3$ is A—COOR$_4$,
A is a direct bond, methylene or ethylene; and
R$_4$ is methyl or alkyl of 12 to 18 carbon atoms.

The R$_1$ and R$_2$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred.

A is preferably ethylene and R$_4$ is preferably methyl, dodecyl and octadecyl.

The compounds of this invention are preferably prepared by reacting the appropriate 2,6-disubstituted phenol with 3,9-dichloro-2,4,8,10-tetraoxa-3,9-diphosphospiro-[5,5]undecane. It has been noted, however, that with this process only moderate yields are obtained even when the phenol is reacted as the phenolate anion in the presence of a polar aprotic solvent such as tetrahydrofuran. Greater efficiency is further required when the phenolic groups are highly hindered by two ortho alkyl groups such as tertiary alkyl groups.

Accordingly, it is a further aspect of this invention to provide an improved preparative procedure for pentaerythritol diphosphites, in general, and the instant diphosphites in particular, whereby the above reactants are reacted in the presence of at least an effective catalytic amount of a mono- or polyalkylene glycol ether catalyst that will render the phenolate anion more reactive and that will complex the counter ions.

Thus, the reaction is reflected in the equation

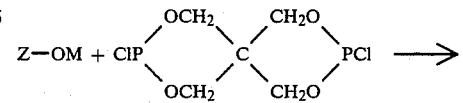

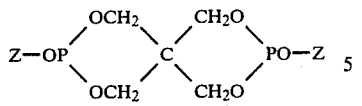

wherein Z is alkyl, alkenyl, cycloalkyl, aryl, aralkyl, or alkanoyl-substituted aryl or each of these groups substituted by hydroxy, alkoxy or halogen; and M is hydrogen or an alkali or alkaline earth metal, with the alkali metal being preferred.

In addition to the compounds of this invention, typical compounds which can be prepared include diphenyl pentaerythritol diphosphite, di-p-tolyl pentaerythritol diphosphite, methyl stearyl pentaerythritol diphosphite, di-2,4-xylenyl pentaerythritol diphosphite, di-t-butylphenyl pentaerythritol diphosphite, methyl oleyl pentaerythritol diphosphite, dimethyl pentaerythritol diphosphite, diethyl pentaerythritol diphosphite, phenyl p-nonylphenyl pentaerythritol diphosphite, dihexyl pentaerythritol diphosphite, dicyclohexyl pentaerythritol diphosphite, phenyl o-dodecylphenyl pentaerythritol diphosphite, didecyl pentaerythritol diphosphite, diisodecyl pentaerythritol diphosphite, methyl eicosanyl pentaerythritol diphosphite, methyl octyl pentaerythritol diphosphite, di-2-chloroethyl pentaerythritol diphosphite, phenyl 2,4-di (nonyl) phenyl pentaerythritol diphosphite, di-2 chloropropyl pentaerythritol diphosphite, di-(4-chlorophenyl) pentaerythritol diphosphite, di(3-chlorophenyl) pentaerythritol diphosphite, di-(2-chlorophenyl) pentaerythritol diphosphite, diallyl pentaerythritol diphosphite, di(2-decenyl) pentaerythritol diphosphite and di-(2,4-di-butylphenyl) pentaerythritol diphosphite.

The preparation of the dichloro reactant is known in the art and generally proceeds by the reaction of pentaerythritol and phosphorus trichloride in a molar ratio of 1:2 to 1:3 in the presence of an inert, nonpolar solvent and, optionally, an amide catalyst. Typical solvents include aromatic hydrocarbons such as benzene, toluene, xylene, and the like, while typical amides include dimethylformamide, dimethylacetamide and 1-methyl-2-pyrrolidinone.

The instant process proceeds by forming a solution of the Z-OM reactant, adding a strong base and the mono- or polyalkylene glycol ether thereto, maintaining the solution at room temperature or heating the solution to a maximum temperature of about 40°–60° C., adding the dichloro pentaerythritol diphosphite generally in its solution form (no necessity to isolate material), allowing the reaction to proceed at a temperature of from about 25° to 50° C. for a period of generally from about 1 to 16 hours and isolating the product.

The reactants are generally present in approximately stoichiometric amounts. The glycol ether catalyst is present in amounts ranging from 1 to 30 mole %, based on the phenol reactant, and preferably 5 to 20 mole %.

Suitable complexing agents are mono- and polyalkylene glycol ethers corresponding to the formula

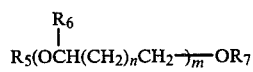

wherein $R_5$, $R_6$ and $R_7$ are independently hydrogen or lower alkyl of 1 to 8 carbon atoms, provided that not more than one of $R_5$ and $R_7$ is hydrogen, n is 0, 1 or 2, and m is 1 to 9, and preferably m is 2 to 5.

Suitable mono- and polyalkylene glycols are ethylene glycol monoethyl ether, ethylene glycol dimethyl ether, diethylene glycol diethyl ether, triethylene glycol dibutyl ether, tripropylene glycol dimethyl ether, tetraethylene glycol dimethyl ether, tetraethylene glycol diethyl ether and pentaethylene glycol monoethyl ether. Triethylene glycol dimethyl ether and tetraethylene glycol dimethyl ether are preferred when the counter ions are sodium or potassium.

Strong bases are preferred for converting the phenol to phenolate ions as noted above. Metal and ammonium hydroxides, hydrides and amides may be used. The hydroxide bases, however, are not indicated for use in the case where the phenol has a hydrolyzable ester group such that formation of the phenolate anion may be accompanied by saponification of the ester group. Sodium hydride was found to be especially applicable in cases susceptible to hydrolysis Solvents which may be utilized include aromatic hydrocarbons such as benzene, toluene, xylene and the like, or a heterocyclic ether such as tetrahydrofuran.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylo nitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxed based on synthetic esters (e.g. phthalates, adipates, phosphates or trimellitates) and also mixtures of synthetic esters with mineral oils in various weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. ANTIOXIDANTS

1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-isobutylphenol
2,6-di-cyclopentyl-4-methylphenol
2-(-methylcyclohexy)-4,6-dimethylphenol
2,6-di-octadecyl-4-methylphenol
2,4,6-tri-cyclohexylphenol
2,6-di-tert.butyl-4-methoxymethylphenol

1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol

1.3. Hydroxylated thiodiphenyl esters, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane)
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)butyrate], di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt

1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate

1.7. Esters of β-(3,5-di-tert.butyl-4-hydroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of β-(5-tert.butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid, for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine

2. UV ABSORBERS AND LIGHT STABILISERS

2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids, for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates for example, α-cyano-62, β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxy-oxanilide, 2,2'-dioctyloxy-5,5'-di-tert.butyl-oxanilide, 2,2'-didodecyloxy-5,5'-di-tert.butyl-oxanilide, 2-ethoxy-2'-ethyloxanilide, N,N'-bis (3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and paramethoxy-as well as of o- and p-ethoxy-disubstituted oxanilides.

3. METAL DEACTIVATORS, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenyl-propionyl)-hydrazine, 3-salicyloylamino-1,2,4-triazole, bis-benzylidene-oxalic acid dihydrazide.

4. PHOSPHITES AND PHOSPHONITES, for example, triphenyl phosphite, diphenylalkyl phosphites, phenyldialkyl phosphites, tri-(nonylphenyl)-phosphite, trilauryl phosphite, trioctadecyl phosphite, di-stearyl-pentaerythritol diphosphite, tris(2,4-di-tert.butylphenyl) phosphite, di-isodecylpentaerythritol diphosphite, di-(2,4-di-tert.butylphenyl)pentaerythritol diphosphite, tristearyl-sorbite triphosphite, tetrakis(2,4-di-tert.butylphenyl)-4,4'-diphenylylendiphosphonite.

5. COMPOUNDS WHICH DESTROY PEROXIDE, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecyl-mercapto)-propionate.

6. POLYAMIDE STABILISERS, for example copper salts in combination with iodides and/or phosphorus compounds and salts of divalent manganese.

7. BASIC CO-STABILISERS, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. NUCLEATING AGENTS, for example, 4-tert.butyl-benzoic acid, adipic acid, diphenylacetic acid.

9. FILLERS AND REINFORCING AGENTS, for example, calcium carbonate, silicates, glass fibres, asbestos, talc, kaolin, mica, barium sulfate, metal oxides and hydroxides, carbon black, graphite.

10. OTHER ADDITIVES, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

Bis(2,6-di-tert-butyl-4-ethylcarboxyoctadecylphenyl) pentaerythritol diphosphite (A)

3,9-dichloro-2,4,8,10-tetraoxa-3,9-diphosphaspiro[5,5]undecane(4)

A dry reaction flask was charged with 7.1 grams (0.051 moles) of pentaerythritol, 70 ml. toluene and 0.36 grams dimethylformamide with stirring. Thereafter, 18.3 grams (0.133 moles) of phosphorus trichloride was added dropwise to the stirred slurry. The reaction mixture was stirred and heated at 25°–60° C. for 5.5 hours at which time the reaction was substantially complete as indicated by the amount of HCl evolved. Excess phosphorus trichloride, hydrogen chloride and about 45 ml toluene were stripped off under pressure (15 to 30 mm Hg).

(B) Toluene dispersion of sodium salt of n-octadecyl 3,5-di-tert-butyl-hydroxyhydrocinnamate A flask containing 75 ml toluene was charged with 4.45 grams (0.11 moles) of sodium hydride and 4.0 grams (0.02 moles) of tetraethyleneglycol dimethyl ether. A solution of 53.1 grams of n-octadecyl 3,5-di-tert-butyl-hydroxyhydrocinnamate in 80 ml of dry toluene at 15°-20° C. was thereafter added over a period of 35 minutes. The reaction temperature warmed to 40° C. over a 15 minute period and was maintained for an additional 1.5 hours. The toluene dispersion was then cooled.

(C) Final Product

Intermediate (A) was added dropwise at 5°-10° C. to intermediate (B) over a 20 minute period. The reaction mixture was stirred at room temperature for two hours, acidified with 1.6 grams of acetic acid and washed with 3×50 ml portions of cold water. The separated organic layer was dried with sodium sulfate and the isolated residue was dissolved in 400 ml isopropanol and allowed to crystallize in an ice water bath. The crystal slurry was filtered and the filter cake washed with cold isopropanol. After drying at 50°-60° C. for four hours at 5-10 mm Hg, 45 grams of a white crystalline powder was obtained, m.p. 86°-89° C.

EXAMPLE 2

Bis-(2.6-di-tert-butyl-4-ethylcarboxymethylphenyl)pentaerythritol diphosphite

The product of Example 2 was prepared by the method of Example 1 by substituting methyl 3,5-di-tert-butyl-4-hydroxyhydrocinnamate for the octadecyl analog of Example 1. The product of Example 2 was isolated as white crystals melting at 235° to 240° C.

EXAMPLE 3

Bis-(2,6-di-tert-butyl-4-ethylcarboxy-n-dodecylphenyl)-pentaerythritoldiphosphite The product of Example 3 was prepared by the method of Example 1 by substituting n-dodecyl 3,5-di-tert-butyl-4-hydroxy-hydrocinnamate for the octadecyl anolog of Example 1. The product of Example 3 was isolated as a white crystalline product, m.p. 78°-81° C., by crystallization from acetonitrile.

EXAMPLE 4

Bis(2,6-di-tert-butyl-4-carboxyoctadecylphenyl)pentaerythritol diphosphite

The product of Example 4 was prepared by the method of Example 1 by substituting n-octadecyl 3,5-di-tert-butyl-4-hydroxybenzoate for the n-octadecyl compound of Example 1. The product was isolated as white crystals, m.p. 84°-99° C.

EXAMPLE 5

Bis(2,6-di-tert-butyl-4-carboxymethylphenyl)pentaerythritol diphosphite

The product of Example 5 was prepared by the method of Example 1 by substituting methyl 3,5-di-tert-butyl-4-hydroxybenzoate for the n-octadecyl compound of Example 1. The product was isolated as white crystals, m.p. 225°-229° C.

EXAMPLE 6

2-(2,6-di-tert-butyl-4-ethylcarboxyoctadecylphenoxy)5,5-dimethyl-1,3,2-dioxaphosphorinane(prior art)

An equivalent amount of 2-chloro-5,5-dimethyl-1,3,2-dioxaphosphorinane (0.07 moles) was added to the toluene dispersion of the sodium salt of n-octadecyl-3,5-di-tert-butyl-4-hydroxyhydrocinnamate (Example 1B) in an analogous manner as described in Example 1C. In this case, an additional 70 ml of toluene were required to obtain a stirrable reaction mixture at 10° C., which was then allowed to react at room temperature overnight. After acidification with acetic acid and clarification by removal of a small amount of insoluble matter, the solvents were removed by distillation at reduced pressure, the crude residue being twice recrystallized from acetone yielding white crystals melting at 80°-82° C.

EXAMPLE 7

2-(2,6-di-tert-butyl-4-ethylcarboxymethylphenoxy)5,5-dimethyl-1,3,2-dioxaphosphorinane (prior art)

The product of Example 7 was made in analogous manner as outlined for the product of Example 6 by substituting methyl 3,5-di-tert-butyl-4-hydroxycinnamate for the octadecyl analog in the procedure of Example 6. The product of Example 7 was isolated as white crystals, m.p. 134°-136° C.

EXAMPLE 8

2-(2,6-di-tert-butyl-4-ethylcarboxy-n-octadecylphenoxy)-1,3,2-dioxaphospholane (prior art)

The compound of Example 8 was made in an analogous manner to the procedure of Example 1C by reacting 2-chloro-1,3,2-dioxaphospholane with a toluene dispersion of the sodium salt of n-octadecyl 3,5-di-tert-butyl-4-hydroxy-hydrocinnamate (Example 1B). After recrystallization from acetone, the compound of this example was isolated as white crystals melting at 54°-56° C.

EXAMPLE 9

Oxidative induction time was determined by ASTM D-3895-80 adapted by substituting an aluminum pan for a copper pan.

Unstablized polypropylene powder (Hercules Profax 6501) was thoroughly blended with 0.3%, by weight, of the various diphosphites and tested for oxidative stability by ASTM method D-3895-80 by being heated in an oxygen atmosphere at an oxygen flow rate of 50 ml/min and a temperature of 200° C. using a DuPont R-90 Thermal Analyzer fitted with the DSC module. Time to failure was determined by means of the oxidative induction time.

The test results are shown in the following table:

| Additive | Oxidative Induction Time (mins.) |
| --- | --- |
| Example 1 | 10 |
| Example 2 | 5 |
| Example 6 | 1 |
| Example 7 | 1 |
| Example 8 | 7 |

The results indicate the improved oxidation stability provided by the compounds of this invention.

EXAMPLE 10

A 10 mg sample of stabilizer was placed in an open platinum boat and the temperature (°C.) to 10% weight loss determined for each sample under a nitrogen atmosphere in a DuPont 951 Thermogravimetric Analyzer.

| Example | Temperature to 10% Weight Loss |
| --- | --- |
| 1 | 365 |
| 6 | 295 |

The compound of this invention again shows to advantage in this test procedure.

EXAMPLE 11

Oxidation stability in a further substrate was determined by charging 60 grams of the base formulation identified below as modified by the indicated additives to a Brabender and mixing at 180° C. The time to increase in torque is recorded as the degradation time, the higher the number the better the performance. The test data is noted in the following table:

| Base Formulation | |
| --- | --- |
| | Parts |
| polyvinyl chloride resin | 100.0 |
| methacrylic acid/ester processing aid | 2.0 |
| acrylic impact modifier | 7.0 |
| calcium stearate | 0.8 |
| polyethylene wax | 0.2 |
| paraffin wax | 1.0 |
| tin mercaptide | 2.0 |

| Additive | Degradation Time (minutes) | % Torque Increase |
| --- | --- | --- |
| 5 phr TiO$_2$ | 39.50 | 0.00 |
| 5 phr TiO$_2$ + 1 phr Ex. 1 | 59.00 | 49.4 |
| 5 phr TiO$_2$ + 1 phr Ex. 6 | 52.50 | 32.9 |

EXAMPLE 12

Hydrolytic stability was determined by the application of thin layer chromatography and infrared spectroscopy as appropriate. A 200 mg sample was weighed into a petri dish and exposed to an atmosphere of 80% relative humidity at room temperature (ca 25° C.). When about a 0.5% to 1% increase in weight was observed, a sample was taken, dissolved in carbon tetrachloride at a concentration of 1% and examined by thin layer chromatography and infrared spectroscopy to determine the residual presence of the stabilizer.

| Stabilizer | Time to Complete Hydrolysis (days) |
| --- | --- |
| Example 1 | No hydrolysis in 260 days |
| Example 7 | No hydrolysis in 224 days |
| Example 8 | Complete hydrolysis in less than 2 days. |

The compound of this invention thus showed to advantage in a further area of importance for a commercial stabilizer compound.

Summarizing, it is seen that this invention provides a novel preparative procedure as well as novel compounds which exhibit effective stabilization activity. Variations may be made in proportions, procedures and materials without departing from the scope of the invention as defined by the following claims.

What is claimed is:

1. In the method for the preparation of a pentaerythritol diphosphite of the formula

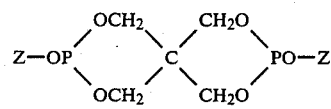

wherein Z is alkyl, alkenyl, aryl, aralkyl, or alkanoyl-substituted aryl or each of these groups substituted by hydroxy, alkoxy or halogen; which comprises reacting at elevated temperatures a compound of the formula Z-OM wherein M is hydrogen or an alkali or alkaline earth metal with 3,9-dichloro-2,4,8,10-tetraoxa-3,9-diphosphaspiro[5,5]undecane in the presence of a solvent and a strong base, the improvement comprising conducting the reaction in the presence of a catalytic amount of a mono- or polyalkylene glycol ether catalyst.

2. The process of claim 1, wherein said mono- or polyalkylene glycol catalyst corresponds to the formula

wherein
R$_5$, R$_6$ and R$_7$ are independently hydrogen or lower alkyl of 1 to 8 carbon atoms, provided that not more than one of R$_5$ and R$_7$ is hydrogen;
n is 0, 1 or 2, and
m is 1 to 9.

3. The process of claim 2, wherein said polyalkylene glycol is triethylene glycol dimethyl ether or tetraethylene glycol dimethyl ether.

4. The process of claim 1, wherein Z-OM is

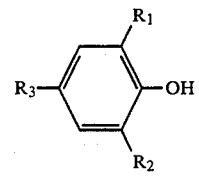

where
R$_1$ and R$_2$ are lower alkyl of 1 to 8 carbon atoms,
R$_3$ is A—COOR$_4$,
A is a direct bond, methylene or ethylene; and
R$_4$ is methyl or alkyl of 12 to 18 carbon atoms.

5. The process of claim 4, wherein Z-OM is n-octadecyl 3,5-di-tert-butyl-hydroxyhydrocinnamate.

6. The process of claim 1, wherein said catalyst is present in a concentration of from 1 to 30 mole % based on the phenol reactant.

* * * * *